United States Patent [19]

George

[11] Patent Number: 4,768,501

[45] Date of Patent: Sep. 6, 1988

[54] METHOD OF WATERPROOF SEALING OF CASTS AND DRESSINGS

[76] Inventor: Frederick W. George, 6009-B Sunrise Blvd., Citrus Heights, Calif. 95610

[21] Appl. No.: 48,214

[22] Filed: May 11, 1987

[51] Int. Cl.⁴ .............................................. A61F 13/00
[52] U.S. Cl. ........................................ 128/82; 128/157
[58] Field of Search ................. 128/90, 132 R, 157, 128/171, DIG. 18, DIG. 20, 156, 82, 83

[56] References Cited

U.S. PATENT DOCUMENTS

| | | | |
|---|---|---|---|
| 3,329,143 | 7/1967 | Gordon | 128/DIG. 18 X |
| 3,659,599 | 9/1969 | McLaughlin | 128/157 |
| 3,785,374 | 1/1974 | Lipson | 128/DIG. 20 X |
| 4,098,268 | 7/1978 | Scott | 128/82 |
| 4,139,003 | 2/1979 | Little | 128/82 |
| 4,639,945 | 2/1987 | Betz | 128/82 X |

Primary Examiner—Alan Cohan

[57] ABSTRACT

The disclosure is of a method of forming a waterproof seal about the cast or dressing on a patient. An air- and water-impervious flexible membrane is placed over the cast or dressing to a position where the membrane's edge margins overlie the patient's skin along the perimeter of the cast or dressing. A vacuum is created between the membrane and skin by evacuating air through a suction tube or valve. The vacuum creates a close, snug fit of the membrane over the entirety of the cast or dressing and over a relatively large surface area of skin to provide a waterproof seal.

8 Claims, 2 Drawing Sheets

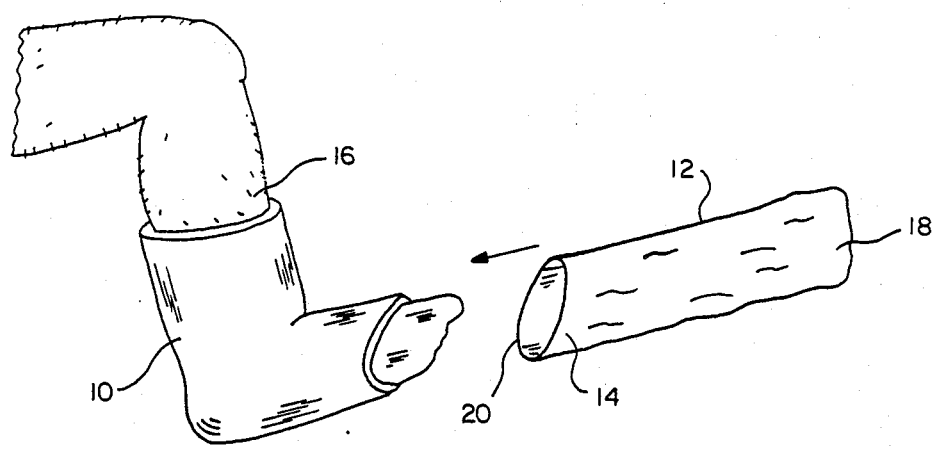
FIG.—1
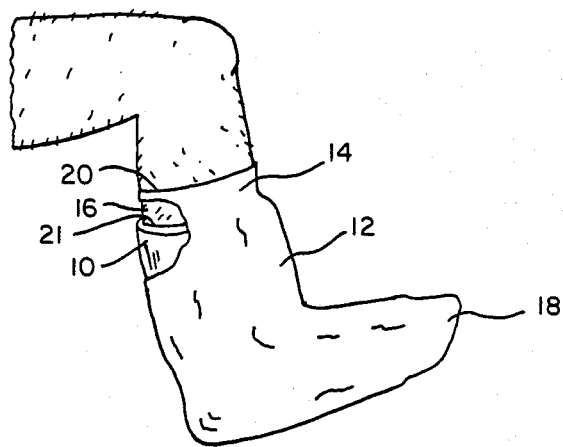
FIG.—2

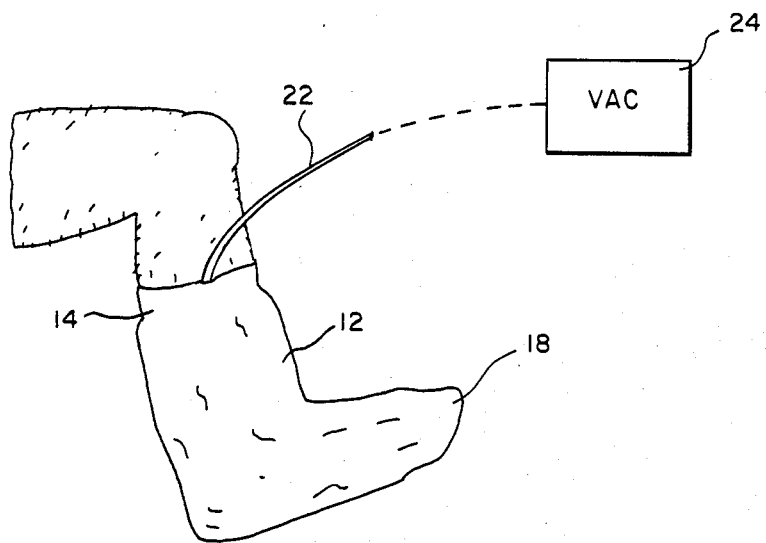
FIG. — 3
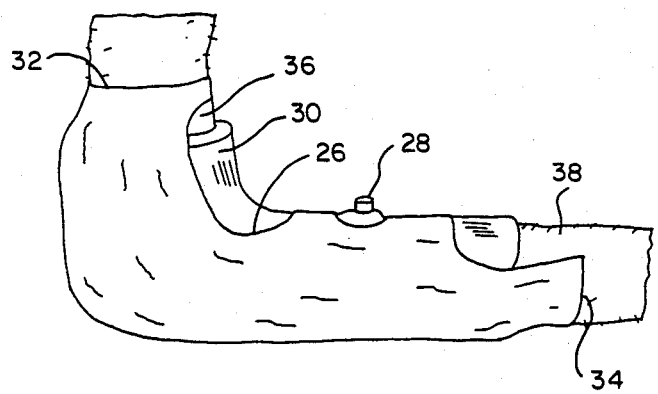
FIG. — 4

METHOD OF WATERPROOF SEALING OF CASTS AND DRESSINGS

BACKGROUND OF THE INVENTION

This invention relates in general to protective coverings in the medical field, and in particular relates to providing waterproof protective coverings for casts, bandages and other dressings on a patient.

A problem frequently encountered in the medical field is in preventing moisture from entering a patient's cast, bandage or other dressing. Such unintended intrusion of moisture can result in degradation of the cast, skin breakdown or wound infection.

The prior art efforts to protect casts and dressings on a patient include flexible coverings of the type shown in U.S. Pat. No. 4,139,003 issued Feb. 13, 1979 to Little. A covering of the type shown in the Little patent provides sealing by a ring forming an elastic constriction over the area of skin adjacent the end of the cast. Among the disadvantages and limitations of this type of protective covering are that there is a relatively small surface area of skin which is sealed by the constricting ring such that water can leak in. Such a covering also has a relatively limited range of adjustability in fitting casts and dressings of a range of sizes and shapes. Furthermore, when in use the loose portion of the covering distal to the constricting ring is baggy such that it is slippery and clumsy and can be hazardous in a bath. The relatively large and baggy nature of the covering also makes it difficult or impossible to use when swimming or in hydrotherapy. Such a protective covering also makes it difficult to detect water leakage while bathing which can result in degradation of the cast, skin breakdown or wound infection.

Another prior art protective covering is disclosed in U.S. Pat. No. 3,659,599 issued May 2, 1972 to McLaughlin. The device of the McLaughlin patent provides a sheath with small pockets acting as suction cups at one end to form a seal to retain moisture in a bandage or dressing of the wet soak type. The pockets cover separate, small areas of skin and are spaced-apart about the end of the sheath to form a dam to prevent moisture from leaking out. This type of protective covering would have disadvantages and limitations similar to those mentioned with respect to the Little patent.

It is an object of the present invention to provide a method of forming a moisture-proof seal about casts or dressings which obviates the disadvantages and limitations of prior art protective coverings in this field.

Another object is to provide a method of forming a waterproof covering for a patient's cast or dressing using a flexible membrane in which portions of the membrane are maintained in a close fit over a relatively large surface area on the skin to provide an effective seal which minimizes moisture leakage.

Another object is to provide a mehtod of the type described in which a range of adjustability of fit is achieved for use with a wide variety of size and shapes of casts and dressings.

Another object is to provide a method of the type described in which a tight fit is formed between the membrane and cast or dressing permitting it to be safely used in the bath, while swimming or in hydrotherapy.

A further object is to provide a method of forming a waterproof covering of the type described in which any water leakage while the covering is in use are reaily detected so that measures can be immediately taken to prevent further harmful moisture intrusion.

The invention in summary comprises a method of waterproof sealing a patient's cast or dressing through the use of a water- and air-impervious flexible membrane. The method includes the steps of placing the membrane over the cast or dressing so that the membrane's edge margin extends over a portion of the patient's skin along a perimeter of the cast or dressing. In the next step a vacuum is formed between the membrane and cast or dressing sufficient to cause atmospheric pressure to force the membrane into sealing contact with the skin and with a snug, close fit with the cast or dressing. In one embodiment the vacuum is formed by inserting a suction tube through the interface between the membrane edge margin and skin and evacuating air through the tube. After the sealing contact between the membrane and skin is formed the suction tube is withdrawn. In another embodiment the vacuum is formed by evacuating air through an air valve which is provided in the membrane.

The foregoing and additional objects and features of the invention will appear from the following specification in which the several embodiments have been described in conjunction with the accompanying drawings.

FIG. 1 is a perspective view of a typical foot cast on a patient, illustrating an initial step in the method of the invention in which the membrane is slipped over the cast.

FIG. 2 is a perspective view similar to FIG. 1 illustrating final positioning of the membrane over the cast.

FIG. 3 is a perspective view similar to FIG. 2 illustrating the step of creating a vacuum between the membrane and cast to form the moisture-proof seal.

FIG. 4 is a perspective view showing another type of cast on a patient illustrating the method of a further embodiment in which air is evacuated through a valve in the membrane.

In the drawings FIGS. 1-3 illustrate sequential steps in the method of one embodiment of the invention for forming a moisture-proof seal about a patient's cast. While the invention will be described in relation to protecting the typical cast 10 on a patient's ankle, it is understood that the invention also has application to protecting various types of casts, bandages and dressings on different extremities of an individual.

The method of the embodiment of FIGS. 1-3 employs the use of a water-and air-impervious flexible membrane 12 of a size and shape suitable for covering the desired cast or dressing. The membrane is sized sufficiently large so that when in place its edge margin 14 extends over the portion 16 of the patient's skin about the perimeter of the end of the cast or dressing. In the example shown for covering the ankle cast, the membrane preferably comprises a tubular sheath having a closed distal end 18 and an open proximal end 20.

Membrane 12 is fabricated of a suitable strong and elastic plastics material which is water- and air-impervious. A latex rubber having a thickness on the order of 0.040" is satisfactory for this purpose. Other materials such as synthetic polymer elastomeric films or sheets could also be employed and the film thickness can be varied depending upon the type of material employed.

In the first step of the method the open end 20 of the sheath is slipped over the patient's foot, as shown in FIG. 1. The sheath is moved along the cast to the position shown in FIG. 2 where its end 20 extends over the portion 16 of the patient's skin about the perimeter of end 21 of the cast. To provide optimum skin sealing area the end 20 is preferably positioned at a distance in the range of 3" to 6" from the end of the cast. In the next step shown in FIG. 3 the end of a small diameter suction tube or hose 22 is inserted through the interface between the sheath's edge margin and the skin. A tube or rubber hose having an outer diameter on the order of ¼" is suitable for this purpose. The opposite end of the tube is connected to a suitable vacuum source 24. The vacuum source is then operated to evacuate air through the tube from the volume underlying the entirety of the sheath. The vacuum which is created causes atmospheric pressure to force the sheath into a snug, tight fit against both the cast and the underlying portions of the patient's skin. The suction tube is then withdrawn from the interface, and the seal which is created between the sheath and skin maintains the vacuum.

With the sheath sealed and in place the cast is protected from moisture intrusion so that the patient can freely bathe, swim or use hydrotherapy. The relatively large surface area of skin which is tightly sealed minimizes moisture leakage. The vacuum causes the sheath to conform with and snugly fit over a wide range of sizes and shapes of casts and dressings. The close fit of the sheath about the cast or dressing eliminates the problem of a loose and slippery covering, making the sheath safe to use in a bath. The force of atmospheric pressure closely presses the sheath against the surface of the cast creating small wrinkles in the sheath which provide some traction for the patient to aid in gripping the covering. The snug fit of the sheath about the cast permits it to be used while swimming or in hydrotherapy, activities that would be difficult or impossible in the case of baggy, loosely-fitting type coverings. When in use any small leaks or moisture intrusion into the sheath are easily detected in that the vacuum is lost and the sheath rapidly becomes loose and baggy. This alerts the patient to the problem so that protective measures can be immediately taken before harmful amounts of water can leak in.

FIG. 4 illustrates the method of another embodiment of the invention for use with a protective membrane 26 provided with an air valve 28. Membrane 26 can be fabricated from the above-described flexible latex material in the form of a sheath sized and shaped to fit over the particular cast or dressing to be protected. This embodiment illustrates, as an example, the method used for a typical lower arm cast 30 in which the membrane comprises a tubular sheath with both its proximal end 32 and distal end 34 open. Air valve 28 comprises a one-way valve, e.g. a check valve, fitted through an opening formed in the sheath.

In the first step of the method of this embodiment sheath 26 is slipped over the cast or dressing to a position where both of its ends extend over the portions 36 and 38 of the patient's skin along the perimeters of opposite ends of the cast. A vacuum source, not shown, is then connected with air valve 28 and air is evacuated from between the sheath and cast. This causes atmospheric pressure to force the sheath into a snug, tight fit about the cast with the membrane's opposite end margins forced into sealing contact with the skin. The vacuum source is then disconnected from the air valve which closes. The seals formed about the skin maintain the vacuum and prevent intrusion of moisture so that the patient is free to bathe, swim or use hydrotherapy.

While the foregoing embodiments are at present considered to be preferred it is understood that numerous variations and modifications may be made therein by those skilled in the art and it is intended to cover in the appended claims all such variations and modifications as fall within the true spirit and scope of the invention.

What is claimed is:

1. A method forming a moisture-proof seal about a cast or dressing on a patient using a water- and air-impervious flexible membrane, the method comprising the steps of placing the membrane over the cast or dressing with the membrane's edge margins extending over the portions of the patient's skin lying along the perimeter edge of the cast or dressing, and creating a vacuum between the membrane and underlying skin sufficient to cause atmospheric pressure to force the membrane edge margins into sealing contact with the skin.

2. A method as in claim 1 in which the membrane is in the form of a sheath having a closed distal end and an open proximal end and in which the cast or dressing is on an extremity of the patient's body, the method including the step of slipping the open proximal end over the patient's extremity to a position where the cast or dressing is covered by the sheath and the edge margin of the proximal ends extends over portions of the patient's skin.

3. A method as in claim 2 in which the edge margin of the proximal end at said position is at a distance in the range of substantially 3" to 6" from said perimeter edge.

4. A method as in claim 1 in which the membrane is in the form of a tubular sheath having an open distal end and an open proximal end, the method including the step of slipping the sheath over the cast or dressing to a position where edge margins of the proximal and distal ends extend over portions of the patient's skin lying along the perimeters of respective ends of the cast or dressing.

5. A method as in claim 4 in which the edge margins of the proximal and distal ends at said position are at distances in the range of substantially 3" to 6" from the perimeter edges of the cast or dressing.

6. A method as in claim 1 in which the step of creating the vacuum comprises the steps of inserting the end of a suction tube through the interface between the membrane's edge margin and the skin, and evacuating air through the tube from between the membrane and skin until the sealing contact of the edge margin is formed with the skin.

7. A method as in claim 6 including the step of withdrawing the suction tube from the interface after the sealing contact is formed with the skin.

8. A method as in claim 1 in which an air valve is provided in the membrane, and the step of creating the vacuum comprises evacuating air through the valve from between the membrane and underlying skin, and closing the valve when the membrane edge is in sealing contact with the skin.

* * * * *